(12) United States Patent
Murthy Aravalli et al.

(10) Patent No.: US 11,779,342 B2
(45) Date of Patent: Oct. 10, 2023

(54) LAPAROSCOPIC PURSE STRING SUTURE DEVICE

(71) Applicant: Covidien LP, Mansfield, MA (US)

(72) Inventors: Avvln Srinivasa Murthy Aravalli, Hyderabad (IN); Rajanikanth Mandula, Hyderabad (IN)

(73) Assignee: Covidien LP, Mansfield, MA (US)

( * ) Notice: Subject to any disclaimer, the term of this patent is extended or adjusted under 35 U.S.C. 154(b) by 487 days.

(21) Appl. No.: 17/117,163

(22) Filed: Dec. 10, 2020

(65) Prior Publication Data

US 2021/0251630 A1    Aug. 19, 2021

Related U.S. Application Data

(60) Provisional application No. 62/978,435, filed on Feb. 19, 2020.

(51) Int. Cl.
| | | |
|---|---|---|
| *A61B 17/11* | (2006.01) | |
| *A61B 17/064* | (2006.01) | |
| *A61B 17/00* | (2006.01) | |
| *A61B 17/072* | (2006.01) | |

(52) U.S. Cl.
CPC ............ *A61B 17/11* (2013.01); *A61B 17/064* (2013.01); *A61B 2017/00004* (2013.01); *A61B 2017/07271* (2013.01); *A61B 2017/1125* (2013.01); *A61B 2017/1142* (2013.01)

(58) Field of Classification Search
CPC .......... A61B 17/11; A61B 2017/07271; A61B 2017/1125; A61B 2017/1142
See application file for complete search history.

(56) References Cited

U.S. PATENT DOCUMENTS

| | | | |
|---|---|---|---|
| 4,821,939 A | * | 4/1989 | Green .................. A61B 17/115 227/19 |
| 4,915,107 A | | 4/1990 | Rebuffat et al. |
| 5,242,457 A | * | 9/1993 | Akopov ............. A61B 17/1114 606/220 |
| 5,484,451 A | | 1/1996 | Akopov et al. |
| 5,891,159 A | | 4/1999 | Sherman et al. |
| 10,806,447 B2 | * | 10/2020 | Kostrzewski .......... A61B 17/42 |
| 2002/0193809 A1 | | 12/2002 | Meade et al. |
| 2012/0037686 A1 | | 2/2012 | Hessler |
| 2017/0181741 A1 | * | 6/2017 | Hessler ............. A61B 17/0482 |
| 2021/0393259 A1 | * | 12/2021 | Haas ...................... A61B 17/29 |

FOREIGN PATENT DOCUMENTS

| | | |
|---|---|---|
| CN | 102228385 A | 11/2011 |
| CN | 102525581 A | 7/2012 |
| CN | 202313536 U | 7/2012 |

(Continued)

OTHER PUBLICATIONS

Extended European Search Report dated Apr. 21, 2021 corresponding to counterpart Patent Application EP 21157925.5.

*Primary Examiner* — Phong Son H Dang
(74) *Attorney, Agent, or Firm* — CARTER, DELUCA & FARRELL LLP (57) ABSTRACT

A surgical device, or a portion of a surgical device, that places purse string sutures in tissue within a body (e.g., intra-peritoneal space). The surgical device includes, or an end effector for a surgical device includes, a jaw assembly, staple cartridges, and a suture.

18 Claims, 6 Drawing Sheets

(56) References Cited

FOREIGN PATENT DOCUMENTS

| | | |
|---|---|---|
| CN | 102824200 A | 12/2012 |
| CN | 103494624 A | 1/2014 |
| CN | 203506794 U | 4/2014 |
| CN | 203564285 U | 4/2014 |
| CN | 203564286 U | 4/2014 |
| CN | 203564287 U | 4/2014 |
| CN | 203564292 U | 4/2014 |
| CN | 203564293 U | 4/2014 |
| CN | 203564294 U | 4/2014 |
| CN | 104434241 A | 3/2015 |
| CN | 104434243 A | 3/2015 |
| CN | 104434244 A | 3/2015 |
| CN | 104434245 A | 3/2015 |
| CN | 104434252 A | 3/2015 |
| CN | 105105820 A | 12/2015 |
| CN | 207785243 U | 8/2018 |
| CN | 208573787 U | 3/2019 |
| CN | 109938789 A | 6/2019 |
| EP | 0598976 A2 | 6/1994 |
| EP | 0625335 A1 | 11/1994 |
| EP | 0632998 A1 | 1/1995 |
| WO | 2008147555 A2 | 12/2008 |

\* cited by examiner

LAPAROSCOPIC PURSE STRING SUTURE DEVICE

CROSS-REFERENCE TO RELATED APPLICATIONS

The present application claims the benefit of and priority to U.S. Provisional Patent Application Ser. No. 62/978,435, filed on Feb. 19, 2020, the entire content of which being hereby incorporated by reference.

TECHNICAL FIELD

The disclosure relates to surgical devices and methods of using the same. More particularly, the disclosure relates to endoscopic surgical devices for affixing purse string sutures to tissue.

BACKGROUND

Surgical stapling apparatus are employed by surgeons to sequentially or simultaneously apply one or more rows of fasteners, e.g., staples or two-part fasteners, to body tissue for the purpose of joining segments of body tissue together and/or creating anastomoses.

Annular surgical stapling apparatus generally include a staple cartridge assembly including annular rows of staples, an anvil assembly operatively associated with the staple cartridge assembly, and an annular blade disposed internal to the annular rows of staples. In use, during an end-to-end circular anastomosis procedure, two ends of hollow tissue sections (e.g., bowels, intestines, or other tubular organs) are positioned between the anvil and staple cartridge assemblies and are joined by clamping the two ends together and driving the annular rows of staples through the clamped tissue sections. During firing of the staples, the annular blade is advanced to cut portions of the tissue sections extending inside the staple lines, thereby establishing a passage through the two stapled tissue sections.

The ends of the tissue sections may be secured over the anvil and staple cartridge assemblies by purse string sutures prior to approximating the anvil assembly relative to the staple cartridge assembly. Purse string sutures are utilized to close or narrow the openings or passages of the tissue sections. A suture is typically passed through each tissue section as a running stitch, in and out around the end of the tissue section, manually or by using an extracorporeal device having a needle or staples for attaching the suture to tissue. After the tissue section is stitched, the ends of the suture are brought together and pulled tight to close or narrow the opening in the tissue section. The ends of the suture may then be tied together.

For example, in laparoscopic gastrointestinal end-to-end anastomosis, a surgeon may create an external incision to bring a tissue section (e.g., intestine or colon) outside of the body in order to secure a purse string suture thereto. The tissue section is devascularized and the purse string suture is attached to the tissue section by hand sewing or using an open purse string device. Such a procedure, however, may cause complications, like bleeding, injury, or increased surgical and/or recovery time, and revascularization of the tissue section may lead to anastomotic leaks.

SUMMARY

According to an aspect of the disclosure, a surgical device includes an end effector including a jaw assembly, first and second staple cartridges, and a suture. The jaw assembly includes first and second jaws disposed in opposed relation relative to each other and movable between an open position and a closed position. The first and second staple cartridges each have a tissue facing surface defining staple pockets retaining staples therein. The first and second staple cartridges are disposed within the first and second jaws, respectively, and are movable therein during movement of the jaw assembly between the open and closed positions. The suture extends longitudinally along the tissue facing surfaces of the staple cartridges and across each of the staple pockets.

The end effector may include a tool assembly, and the first and second jaws may be releasably attached to the tool assembly. The tool assembly may include first and second jaw members, and each of the first and second jaws may include a proximal portion configured to releasably engage a respective one of the first and second jaw members of the tool assembly.

Each of the first and second jaws may extend along a longitudinal axis, and the first and second staple cartridges may be movable along a transverse axis that is orthogonal to the longitudinal axis.

Each of the first and second jaws may include a body defining an elongated support channel and a longitudinally extending rib defining an outer surface of the body. The first and second staple cartridge may be disposed within the respective elongated support channel of the first and second jaws such that when the first and second jaws are in the open position, the first and second staple cartridges are disposed in spaced relation relative to the respective longitudinally extending rib and when the first and second jaws are in the closed position, the first and second staple cartridges abut the longitudinally extending rib.

Each of the first and second staple cartridges may include a staple pusher extending longitudinally thereacross such that when the first and second jaws are in the closed position, the longitudinally extending rib engages the staple pusher to expel the staples from the respective first and second staple cartridges.

Each of the first and second jaws may include a pair of openings defined in the outer surface of the body on opposed sides of the longitudinally extending rib. Each of the first and second staple cartridges may include side walls having a pair of raised edges extending upwardly from the cartridge body on opposed sides of the staple pusher. The pair of raised edges may extend through the pair of openings of the body of the respective first and second jaws.

Each of the first and second jaws may include an inner surface, and when the first and second jaws are in the open position, the tissue facing surface of each of the first and second staple cartridges is offset from the inner surface, and when the first and second jaws are in the closed position, the tissue facing surface is flush with the inner surface.

The suture may include end portions extending distally beyond the first and second staple cartridges and a central portion extending proximally of the first and second staple cartridges, the central portion bending between the first and second jaws.

According to another aspect of the present disclosure, an end effector includes a jaw assembly, first and second staple cartridges, and a suture. The jaw assembly includes first and second jaws disposed in opposed relation relative to each other and movable between an open position and a closed position. The first and second staple cartridges each have a tissue facing surface defining staple pockets retaining staples therein. The first and second staple cartridges are disposed within the first or second jaws, respectively, and are movable therein during movement of the jaw assembly between the open and closed positions. The suture extends longitudinally along the tissue facing surfaces of the first and second staple cartridges and across each of the staple pockets.

The end effector may include a tool assembly, and the first and second jaws may be releasably attached to the tool assembly. The tool assembly may include first and second jaw members, and each of the first and second jaws may include a proximal portion configured to releasably engage a respective one of the first and second jaw members of the tool assembly.

Each of the first and second jaws may extend along a longitudinal axis, and the first and second staple cartridges may be movable along a transverse axis that is orthogonal to the longitudinal axis.

Each of the first and second jaws may include a body defining an elongated support channel and a longitudinally extending rib defining an outer surface of the body. The first and second staple cartridges may be disposed within the respective elongated support channel of the first and second jaws such that when the first and second jaws are in the open position, the first and second staple cartridges are disposed in spaced relation relative to the respective longitudinally extending rib and when the first and second jaws are in the closed position, the first and second staple cartridge abut the longitudinally extending rib.

Each of the first and second staple cartridges may include a staple pusher extending longitudinally thereacross such that when the first and second jaws are in the closed position, the longitudinally extending rib engages the staple pusher to expel the staples from the respective first and second staple cartridges.

Each of the first and second jaws may include a pair of openings defined in the outer surface of the body on opposed sides of the longitudinally extending rib. Each of the first and second staple cartridges may include side walls having a pair of raised edges extending upwardly from the cartridge body on opposed sides of the staple pusher. The pair of raised edges may extend through the pair of openings of the body of the respective first and second jaws.

Each of the first and second jaws may include an inner surface, and when the first and second jaws are in the open position, the tissue facing surface of each of the first and second staple cartridges is offset from the inner surface, and when the first and second jaws are in the closed position, the tissue facing surface is flush with the inner surface.

The suture may include end portions extending distally beyond the first and second staple cartridges and a central portion extending proximally of the first and second staple cartridges, the central portion bending between the first and second jaws.

Other aspects, features, and advantages will be apparent from the description, drawings, and the claims.

BRIEF DESCRIPTION OF THE DRAWINGS

Various aspects of the disclosure are described herein below with reference to the drawings, which are incorporated in and constitute a part of this specification, wherein.

DETAILED DESCRIPTION

The disclosure is directed to surgical devices for placing purse string sutures in tissue within a body (e.g., intra-peritoneal space) without creating an external incision and exteriorizing the tissue as required of open purse string devices or techniques. This can reduce the likelihood of vascular damage to healthy tissue. Further, exteriorization of the tissue during a laparoscopic procedure requires the pneumoperitoneum to be removed and thus, the advantages of having a laparoscopic procedure are not fully realized. Accordingly, intra-peritoneal purse string suture formation allows the patient and the surgeon to get the benefits of laparoscopic surgery.

The surgical devices of the disclosure can reach the low or ultra-low distal stump and form the purse string therein and thus, reduce leaks at the distal stump associated with dog ears that may form during straight staple line purse string operations. The surgical devices of the disclosure minimize or avoid unintended cuts to the tissue that may occur during manual suturing techniques, and provide standard and/or controlled suturing thickness through the tissue.

Embodiments of the disclosure are discussed herein below in terms of surgical devices for securing sutures to tissue. The surgical devices described herein may be used to apply a suture to a hollow or tubular tissue section (also referred to herein, generally, as tissue) by grasping an end portion of the tissue between first and second jaws of the surgical device and securing the suture thereto with staples.

Embodiments of the surgical devices will now be described in detail with reference to the drawing figures wherein like reference numerals identify similar or identical elements. Throughout this description, the term "proximal" refers to a portion of a device, or component thereof, that is closer to a user, and the term "distal" refers to a portion of the device, or component thereof, that is farther from the user. The terms "generally" and "substantially" shall be understood to be words of approximation that take into account relatively little to no variation in the modified term(s). Directional reference terms, such as "upper," "lower," "top," "bottom," "side," and the like, are intended to ease description of the embodiments and are not intended to have any limiting effect on the ultimate orientation of a device or any parts thereof.

Figure 1:
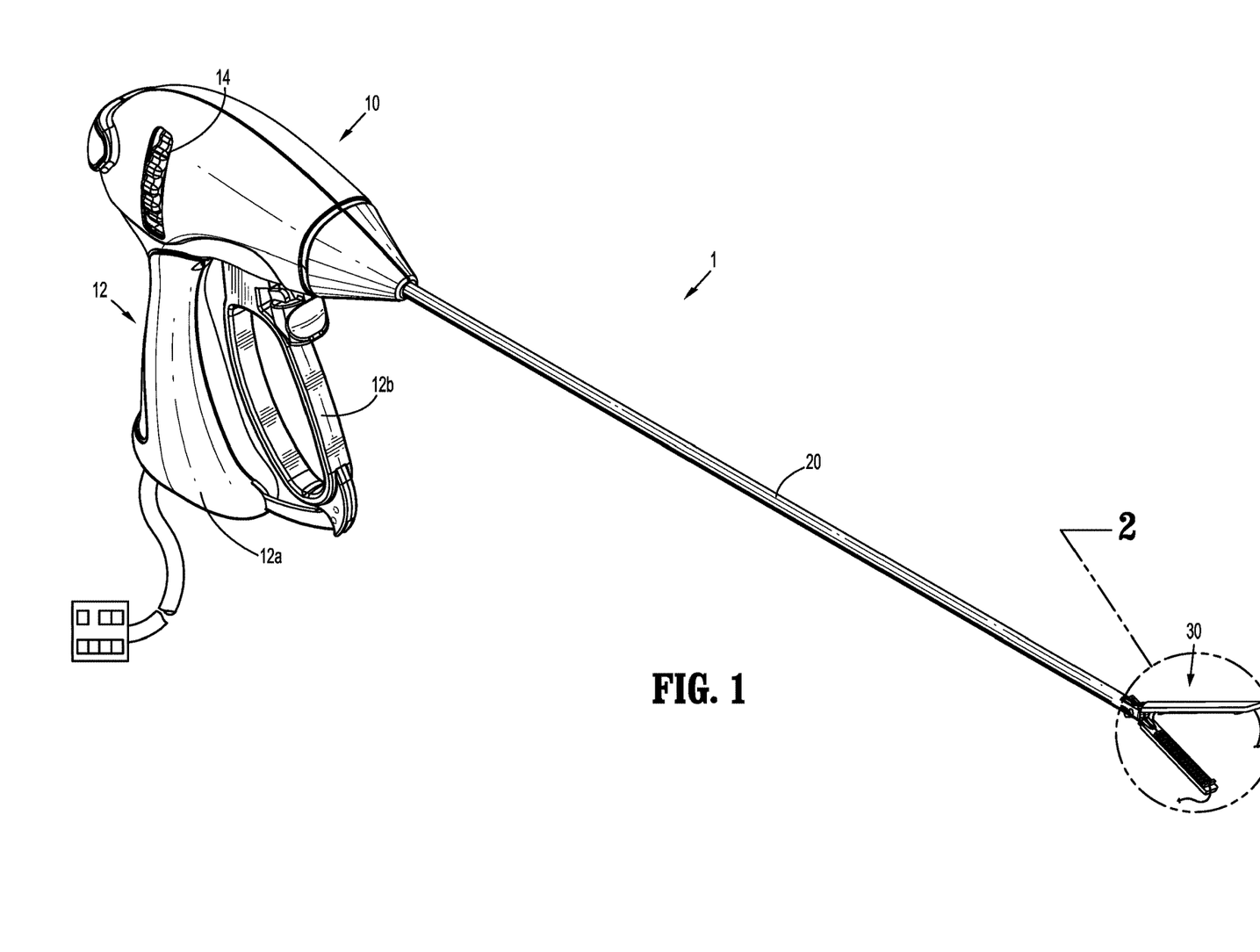
FIG. 1 is a side, perspective view of a surgical device in accordance with an embodiment of the disclosure.
Figure 2:
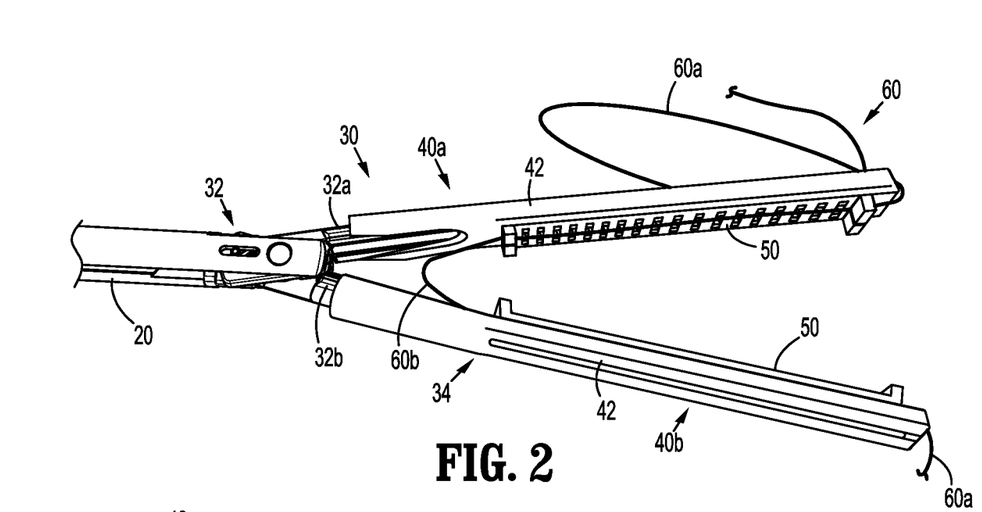
FIG. 2 is an enlarged, perspective view of the area of detail in FIG. 1 of an end effector of the surgical device.

FIGS. 1 and 2 show a laparoscopic purse string suturing device or surgical device 1 for applying purse string sutures to tissue. The surgical device 1 generally includes a housing 10, an elongate body portion or shaft 20 extending distally from the housing 10, and an end effector 30 extending distally from the shaft 20. The end effector 30 includes a tool assembly 32 having opposed jaw members 32a, 32b, and a jaw assembly 34 extending distally from the tool assembly 32. The jaw assembly 34 includes an upper or first jaw 40a and a lower or second jaw 40b disposed in opposed relation relative to the first jaw 40a. The first and second jaws 40a, 40b of the jaw assembly 34 are individually and releasably attached to jaw members 32a, 32b of the tool assembly 32 (e.g., releasably securable to an existing, integral end effector as shown, for example, in FIGS. 1 and 2). Alternatively, the first and second jaws 40a, 40b may be integral with the end effector 30 that, in turn, may be permanently or releasably secured to the shaft 20 of the surgical device 1.

Figure 6:
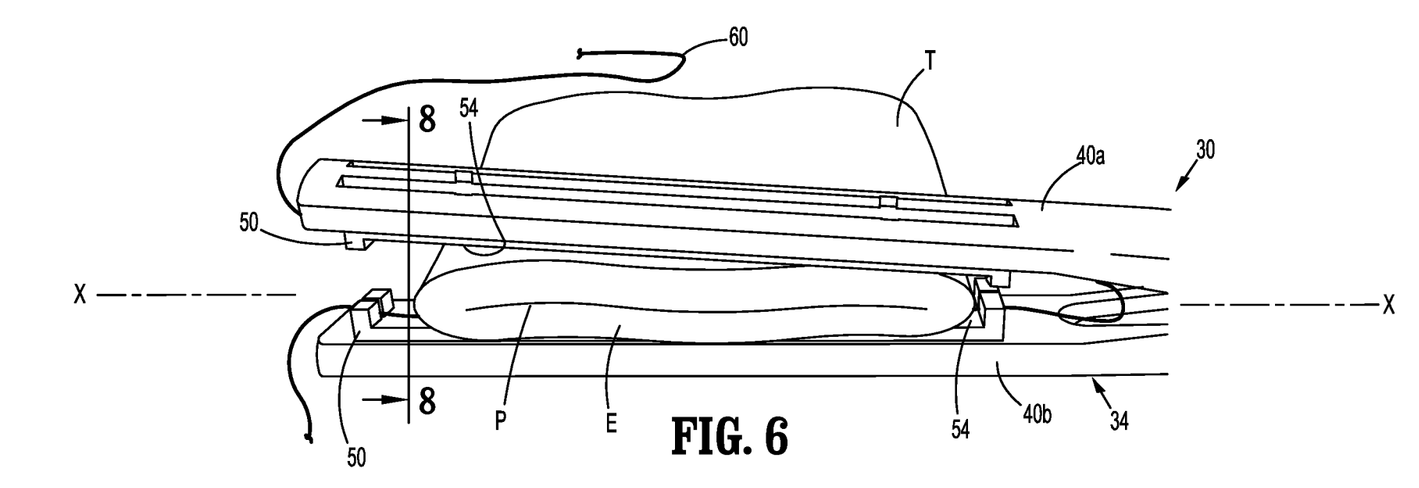
FIG. 6 is a side, perspective view of the jaw assembly of FIG. 2, shown in an open position with tissue positioned between first and second jaws of a jaw assembly during a surgical suturing procedure in accordance with an embodiment of the disclosure.
Figure 7:
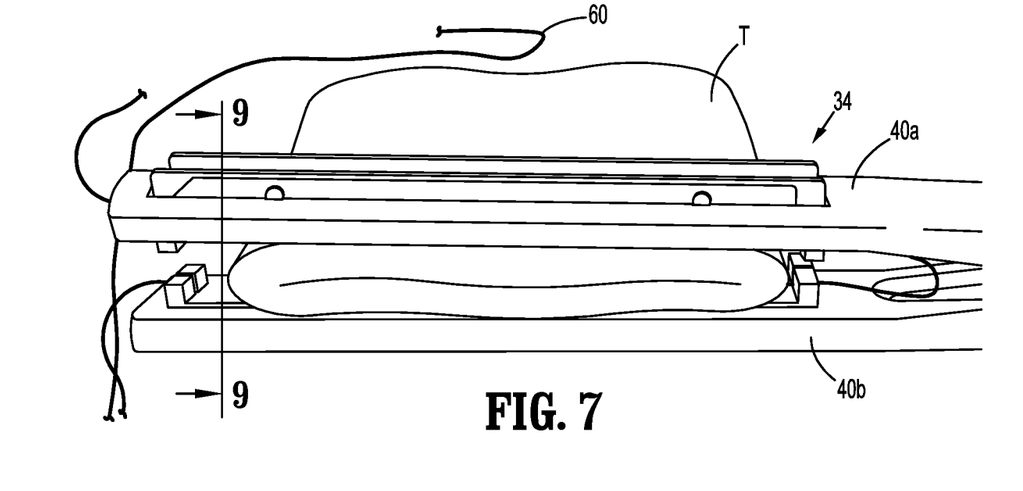
FIG. 7 is a side, perspective view of the jaw assembly of FIG. 6, shown in a closed position with the tissue clamped between the first and second jaws.

The housing 10 of the surgical device 1 includes a handle assembly 12 having a stationary or fixed handle portion 12a and a movable handle portion or trigger 12b that is movable relative to the fixed handle portion 12a to actuate the end effector 30 from an open or unclamped position where the first and second jaws 40a, 40b are disposed in spaced relation relative to each other (see e.g., FIG. 6) and a closed or clamped position where the first and second jaws 40a, 40b are substantially adjacent each other and cooperate to grasp tissue therebetween (see e.g., FIG. 7). Actuation of the trigger 12b applies a suture 60 to tissue captured between the first and second jaws 40a, 40b of the jaw assembly 34, as described in further detail below. A rotation assembly 14 is disposed within the housing 10 to facilitate rotation of the shaft 20 and thus, the end effector 30 so as to properly orient the jaw assembly 34 relative to tissue to be sutured.

Figure 3:
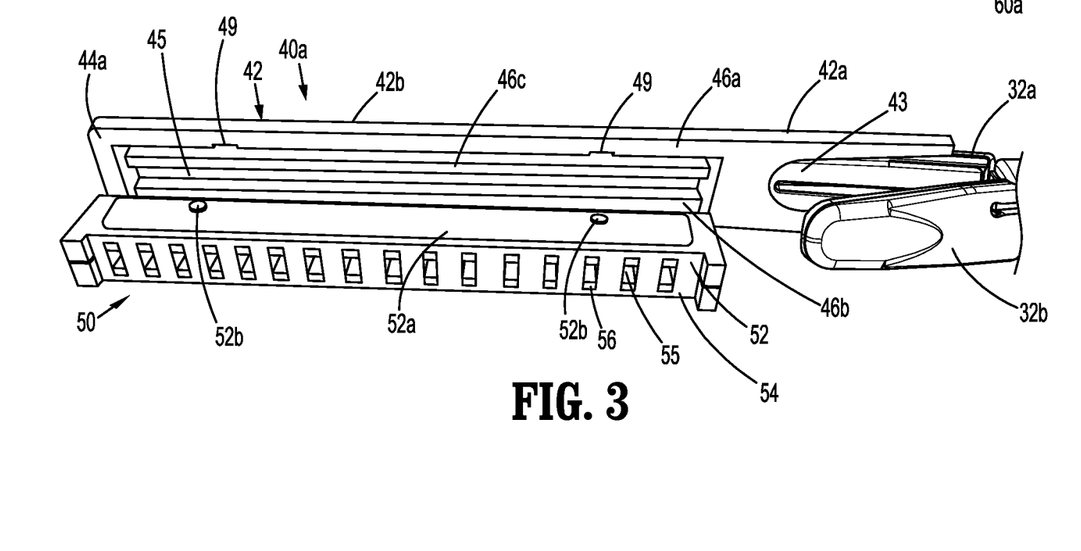
FIG. 3 is a bottom, perspective view of the end effector of FIG. 2, shown with a first jaw of a jaw assembly attached and a second jaw of the jaw assembly removed, and a staple cartridge separated from the first jaw.
Figure 4:
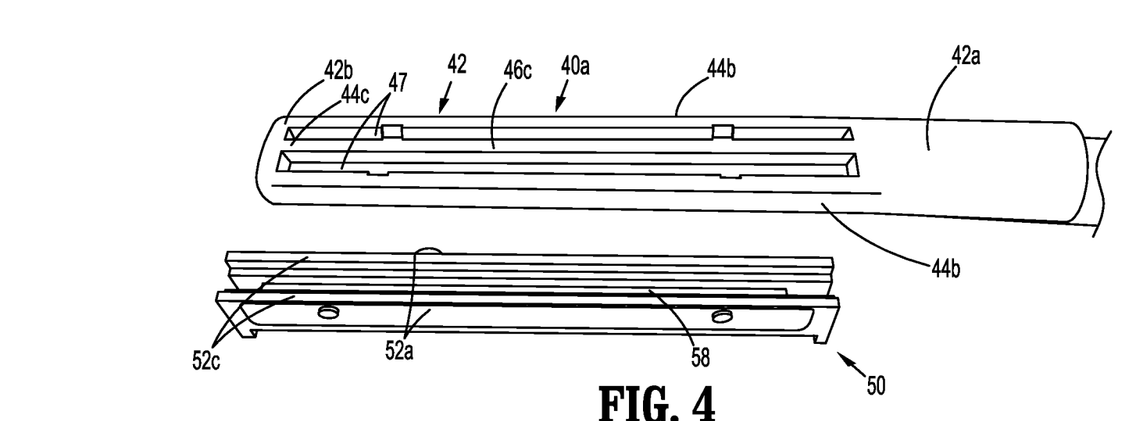
FIG. 4 is a top, perspective view of the first jaw and the staple cartridge of FIG. 3.

As shown in FIGS. 2-4, each of the first and second jaws 40a, 40b includes a body 42 and a staple cartridge 50 disposed within the body 42. While only the first jaw 40a is shown in FIGS. 3 and 4, it should be understood that the second jaw 40b is identical thereto. The body 42 of each of the first and second jaws 40a, 40b has a proximal portion 42a configured to releasably engage the respective jaw member 32a, 32b of the tool assembly 32. The proximal portion 42a of the body 42 includes a slot 43 sized and shaped to receive the jaw member 32a, 32b therein in an interference (e.g., friction) fit arrangement, however, it should be understood that the proximal portion 42a of the body 42 may be coupled to the jaw member 32a, 32b by other mechanical or non-mechanical connectors such as, for example, coupling sheaths and/or temporary adhesives. Further, while the tool assembly 32 is shown as opposed jaw members 32a, 32b having electrically conductive tissue contacting surfaces to perform other functions when the jaw assembly 34 is not secured to the tool assembly 32, it should be understood that the tool assembly 32 may have other configurations as is within the purview of those skilled in the art, and the proximal portion 42a of the body 42 of the first and/or second jaw 40a, 40b may be configured for attachment thereto.

The body 42 of each of the first and second jaws 40a, 40b has a distal portion 42b defining an elongated support channel 45 configured and dimensioned to selectively receive the staple cartridge 50 therein. The staple cartridge 50 can be removable and replaceable within the body 42. The elongated support channel 45 is open at an inner surface 44a of the body 42 and is defined between two longitudinally extending arms 46a, 46b defining opposed side surfaces 44b of the body 42 and a longitudinally extending rib 46c defining a top surface 44c of the body 42. A pair of openings 47 are defined in the top surface 44c of the body 42 on opposed sides of the longitudinally extending rib 46c in a substantially parallel arrangement. The longitudinal extending rib 46c and the pair of openings 47 extend the same length as the longitudinally extending arms 46a, 46b.

The staple cartridge 50 includes a cartridge body 52 having a tissue facing or contacting surface 54 defining staple pockets or retention slots 55 therein for receiving a plurality of fasteners or staples 56 therein. The staple pockets 55 extend transversely across the tissue facing surface 54 such that the staples 56 are disposed in a generally parallel arrangement with respect to each other along the length of the cartridge body 52. The staples 56 are formed from biocompatible materials (e.g., metals or polymers) which may be bioabsorbable or non-absorbable, natural or synthetic, or combinations thereof. The staples 56 are sized to engage a layer of tissue disposed adjacent to the tissue facing surface 54 of the staple cartridge 50. The staples 56 have a substantially U-shaped or C-shaped initial configuration when disposed within the staple pockets 55 that may be deformed to a D-shaped or B-shaped configuration upon firing into tissue.

A staple pusher 58 extends across the staple cartridge 50 and is aligned with backspans 56a (FIG. 10) of the staples 56. The staple cartridge 50 further includes side walls 52a having protrusions 52b extending laterally therefrom, and a pair of raised edges 52c extending upwardly from the cartridge body 52 on opposed sides of the staple pusher 58. The staple cartridge 50 is positioned within the elongated support channel 45 of the body 42 by aligning the protrusions 52b with grooves 49 defined in the longitudinally extending arms 46a, 46b of the body 42 and inserting the staple cartridge 50 therein such that the pair of raised edges 52b extend through the pair of openings 47 defined in the body 42, the staple pusher 58 is disposed adjacent to the longitudinally extending rib 46c of the body 42, and the tissue facing surface 54 is disposed adjacent to the inner surface 44a of the body 42. The staple cartridge 50 is positioned within the body 42 such that it can move or be allowed to move in an upward direction (e.g., outwardly and away from tissue positioned adjacent to the tissue facing surface 54 of the staple cartridge 50) during compression or firing of the surgical device 1. In the unclamped position, the protrusions 52b of the staple cartridge 50 are disposed within the grooves 49 of the body 42 (see e.g., FIG. 8), and in the clamped position, the protrusions 52b of the staple cartridge 50 extend out of the grooves 49 and above the body 42 (see e.g., FIG. 9).

Figure 5:
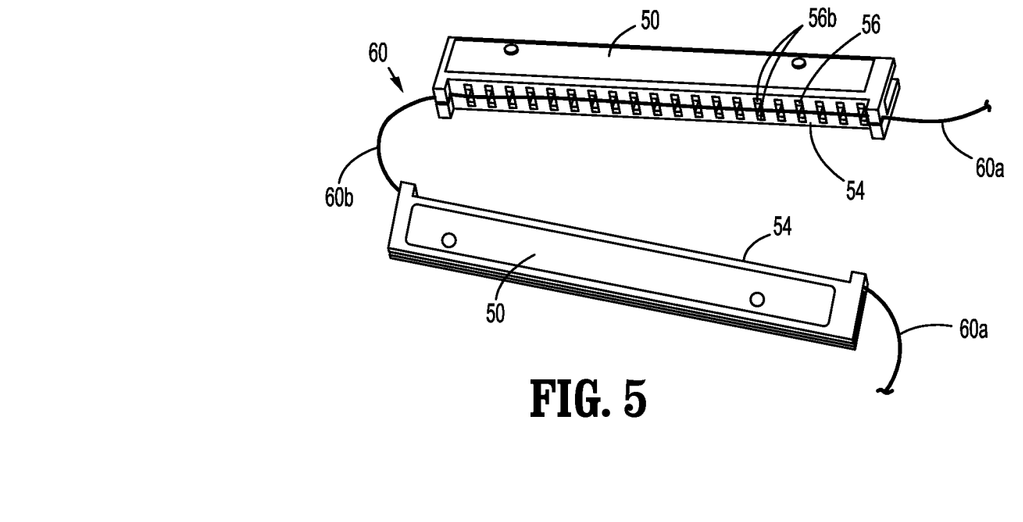
FIG. 5 is a side view of staple cartridges and a suture of the end effector of FIG. 2, shown with first and second jaws of a jaw assembly removed.

As seen in FIGS. 2 and 5, a single strand of suture 60 extends longitudinally along the tissue facing surface 54 of each of the staple cartridges 50 of the first and second jaws 40a, 40b and across each of the staple pockets 55 such that the suture 60 extends between the legs 56b of each of the staples 56 of the staple cartridges 50. The suture 60 may be a monofilament or multi-filament thread formed from biocompatible materials which may be bioabsorbable or non-absorbable, natural or synthetic, or combinations thereof. End portions 60a of the suture 60 extend distally beyond the staple cartridges 50 and the first and second jaws 40a, 40b, and a central portion 60b of the suture 60 extends proximally of the staple cartridges 50 and forms a bend in the suture 60 between the first and second jaws 40a, 40b. The suture 60 may further include a pledget (not shown) at one or both ends portions 60a of the suture 60 to facilitate grasping and/or knotting of the suture 60.

To use the surgical device 1 during a surgical suturing procedure (e.g., to apply a purse string suture to tissue), the end effector 30, which is secured to the distal end of the shaft 20 and loaded with the first and second jaws 40a, 40b, the staple cartridges 50, and the suture 60, as shown in FIGS. 1 and 2, is inserted through an access device (not shown), such as a trocar, a cannula, or an access port, and positioned at a desired surgical site. Tissue "T" (e.g., a hollow tissue section) is placed between the first and second jaws 40a, 40b of the end effector 30, as shown in FIG. 6, with an opening "P" defined through the tissue "T" positioned substantially perpendicular to a central longitudinal axis "X" of the end effector 30 and the open end "E" of the tissue "T" extending laterally adjacent to the side of the end effector 30. Once properly oriented and positioned, surgical device 1 is fired by actuating the trigger 12b (FIG. 1) of the handle assembly 12 such that the jaw assembly 34 is moved from the open position, shown in FIG. 6, to the closed position, shown in FIG. 7. As the first and second jaws 40a, 40b move from the open position to the closed position, the tissue contacting surfaces 54 of the staple cartridges 50 of the first and second jaws 40a, 40b grip the tissue "T" and compress the opening "P" in the tissue "T" closed.

Figure 8:
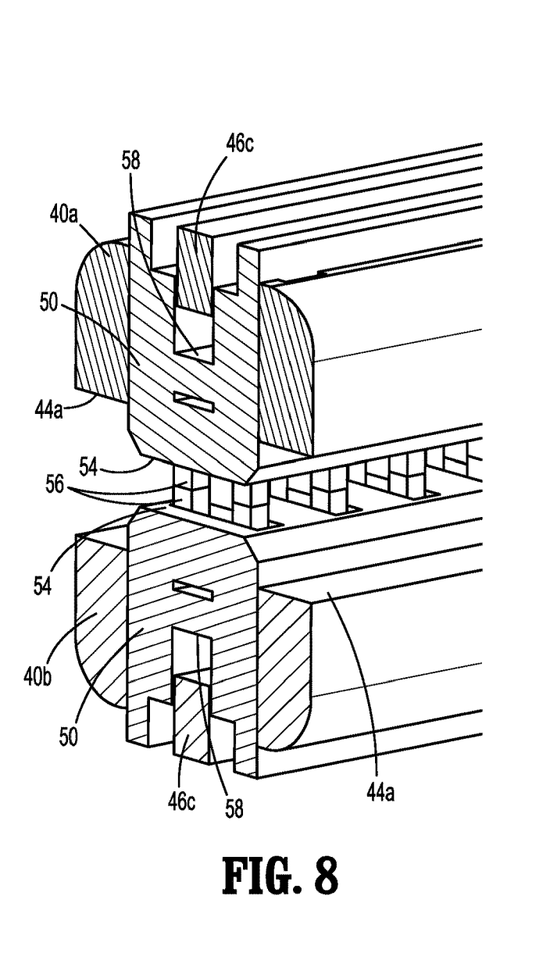
FIG. 8 is a cross-sectional view of the jaw assembly of FIG. 6, shown with the tissue removed, taken along section line 8-8 of FIG. 6.
Figure 9:
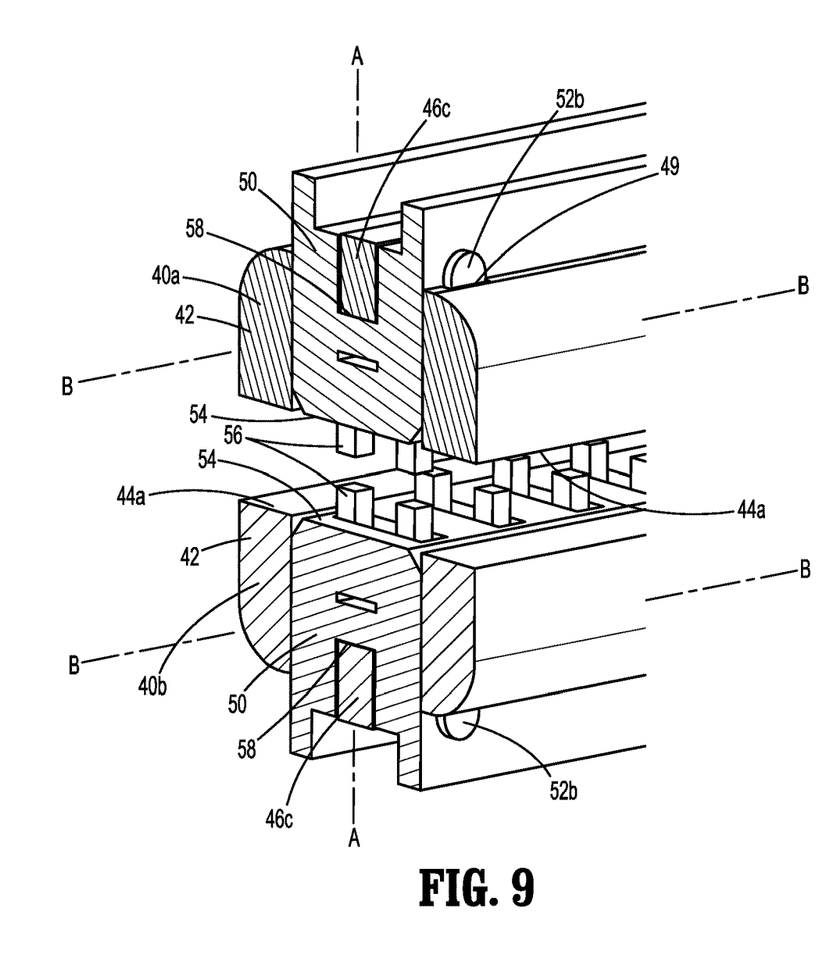
FIG. 9 is a cross-sectional view of the jaw assembly of FIG. 7, shown with the tissue removed, taken along section line 9-9 of FIG. 7.

As shown in FIG. 8, in the open position, the staple pushers 58 of the staple cartridges 50 are disposed in spaced relation relative to the longitudinally extending rib 46c of the respective first and second jaws 40a, 40b, and the tissue facing surfaces 54 of the staple cartridges 50 are offset with respect to the inner surface 44a of the respective first and second jaws 40a, 40b. Alternatively, the staple pusher 58 may touch the longitudinal extending rib 46 prior to clamping and/or firing. During movement from the open position, shown in FIG. 8, to the closed position, shown in FIG. 9, the staple cartridges 50 move outwardly away from the tissue "T" (FIG. 7) during compression, in the direction of transverse axis "A" that is substantially orthogonal to a longitudinal axis "B" extending through each of the first and second jaws 40a, 40b. As the staple cartridges 50 move outwardly, the staple pushers 58 abut the longitudinally extending ribs 46c and the tissue facing surfaces 54 are generally flush with the inner surfaces 44a of the first and second jaws 40a, 40b. The longitudinally extending rib 46c of each of the first and second jaws 40a, 40b acts as a stopper to stop the upward movement of the staple cartridges 50 within the respective first and second jaws 40a, 40b and to push the staple pusher 58 down towards the tissue "T" and fire the staples 56 into the tissue "T."

Figure 10:
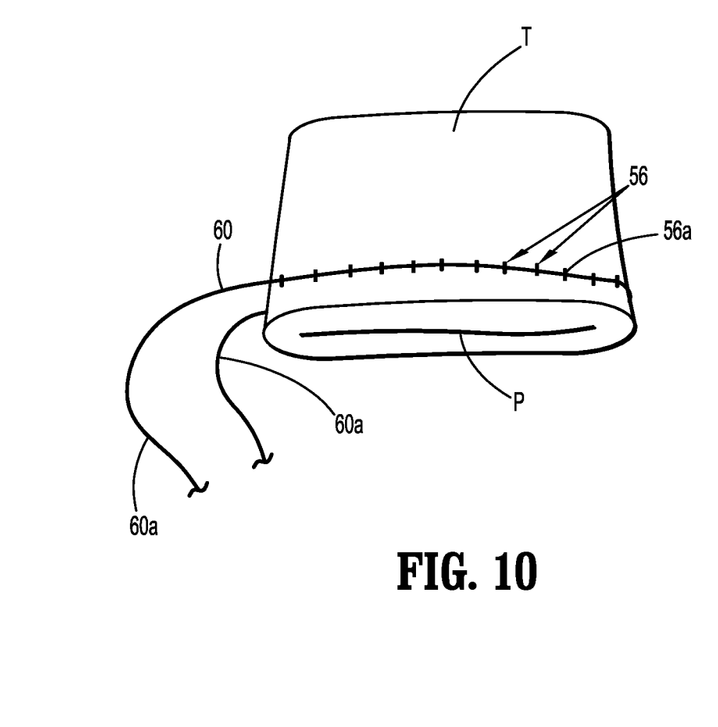
FIG. 10 is a top, perspective view of the tissue of FIGS. 6 and 7, after performing the surgical suturing procedure.
Figure 11:
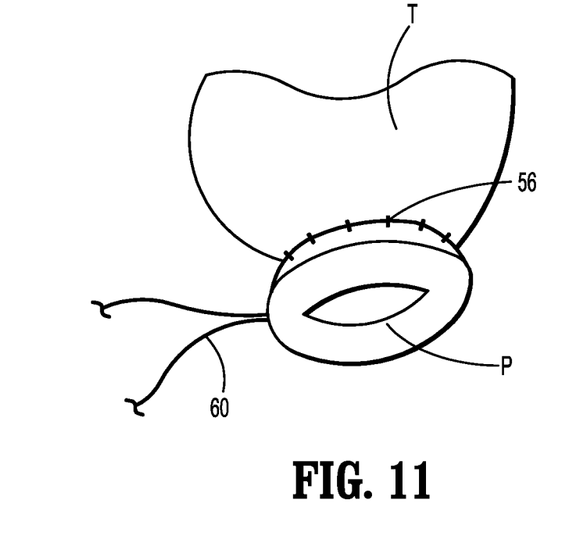
FIG. 11 is a top, perspective view of the tissue of FIG. 10, after tightening a suture stapled to the tissue.

Thereafter, when the first and second jaws 40a, 40b are opened to release the tissue "T," the suture 60 is stapled to the tissue "T," leaving the suture 60 attached to the tissue "T" between each of the formed staples 56 around the perimeter of the tissue "T" (e.g., as a running stitch), as shown in FIG. 10. The end portions 60a of the suture 60 can then be pulled to tighten the suture 60 and narrow the opening "P" defined in the tissue "T," such as around an anvil or cartridge assembly (not shown) of a circular stapler, as shown in FIG. 11.

The end effector 30 may be a single use or reusable end effector. The end effector 30 may be pre-loaded with the jaw assembly 34, with or without the staple cartridges 60 and/or the suture 66 loaded into the jaw assembly 34. The staple cartridges 60 may be manufactured to include the suture 66 loaded therethrough (see e.g., FIG. 5). The jaw assembly 34 may be a fixed, permanent component of the end effector 30 or an interchangeable, releasably engaged part thereof (e.g., securable to an existing end effector or surgical device), and/or the staple cartridges 50 and suture 60 may be replaceable components of the end effector 30.

The end effectors 30 and/or jaw assemblies 34 described herein may also be configured for use with other surgical apparatus, such as robotic, powered, or manual surgical devices/instruments.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the disclosure, and that such modifications and variations are also intended to be included within the scope of the disclosure. Accordingly, the subject matter of the disclosure is not to be limited by what has been particularly shown and described.

What is claimed is:

1. A surgical device comprising:
an end effector including:
a jaw assembly including first and second jaws disposed in opposed relation relative to each other and movable between an open position and a closed position;
first and second staple cartridges each having a tissue facing surface defining staple pockets retaining staples therein, the first and second staple cartridges disposed within the first and second jaws, respectively, and movable therein during movement of the jaw assembly between the open and closed positions; and
a suture extending longitudinally along the tissue facing surfaces of the first and second staple cartridges and across each of the staple pockets, wherein the suture includes end portions extending distally beyond the first and second staple cartridges and a central portion extending proximally of the first and second staple cartridges, the central portion bending between the first and second jaws.

2. The surgical device of claim 1, wherein the end effector includes a tool assembly, and the first and second jaws are releasably attached to the tool assembly.

3. The surgical device of claim 2, wherein the tool assembly includes first and second jaw members, and each of the first and second jaws includes a proximal portion configured to releasably engage a respective one of the first and second jaw members of the tool assembly.

4. The surgical device of claim 1, wherein each of the first and second jaws extends along a longitudinal axis, and the first and second staple cartridges are movable along a transverse axis that is orthogonal to the longitudinal axis.

5. The surgical device of claim 1, wherein each of the first and second jaws includes a body defining an elongated support channel and a longitudinally extending rib defining an outer surface of the body, the first and second staple cartridges disposed within the respective elongated support channel of the first and second jaws such that when the first and second jaws are in the open position, the first and second staple cartridges are disposed in spaced relation relative to the respective longitudinally extending rib and when the first and second jaws are in the closed position, the first and second staple cartridges abut the longitudinally extending rib.

6. The surgical device of claim 5, wherein each of the first and second staple cartridges includes a staple pusher extending longitudinally thereacross, and when the first and second jaws are in the closed position, the longitudinally extending rib engages the staple pusher to expel the staples from the respective first and second staple cartridges.

7. The surgical device of claim 5, wherein each of the first and second jaws includes a pair of openings defined in the outer surface of the body on opposed sides of the longitudinally extending rib.

8. The surgical device of claim 7, wherein each of the first and second staple cartridges includes side walls having a pair of raised edges extending upwardly from the cartridge body on opposed sides of the staple pusher, the pair of raised edges extending through the pair of openings of the body of the respective first and second jaws.

9. The surgical device of claim 1, wherein each of the first and second jaws includes an inner surface, and when the first and second jaws are in the open position, the tissue facing surface of each of the first and second staple cartridges is offset from the inner surface, and when the first and second jaws are in the closed position, the tissue facing surface is flush with the inner surface.

10. An end effector comprising:
   a jaw assembly including first and second jaws disposed in opposed relation relative to each other and movable between an open position and a closed position;
   first and second staple cartridges each having a tissue facing surface defining staple pockets retaining staples therein, the first and second staple cartridges disposed within the first and second jaws, respectively, and movable therein during movement of the jaw assembly between the open and closed positions; and
   a suture extending longitudinally along the tissue facing surfaces of the first and second staple cartridges and across each of the staple pockets, wherein the suture includes end portions extending distally beyond the first and second staple cartridges and a central portion extending proximally of the first and second staple cartridges, the central portion bending between the first and second jaws.

11. The end effector of claim 10, further comprising a tool assembly, and the first and second jaws are releasably attached to the tool assembly.

12. The end effector of claim 11, wherein the tool assembly includes first and second jaw members, and each of the first and second jaws includes a proximal portion configured to releasably engage a respective one of the first and second jaw members of the tool assembly.

13. The end effector of claim 10, wherein each of the first and second jaws extends along a longitudinal axis, and the first and second staple cartridges are movable along a transverse axis that is orthogonal to the longitudinal axis.

14. The end effector of claim 10, wherein each of the first and second jaws includes a body defining an elongated support channel and a longitudinally extending rib defining an outer surface of the body, the first and second staple cartridges disposed within the respective elongated support channel of the first and second jaws such that when the first and second jaws are in the open position, the first and second staple cartridges are disposed in spaced relation relative to the respective longitudinally extending rib and when the first and second jaws are in the closed position, the first and second staple cartridges abut the longitudinally extending rib.

15. The end effector of claim 14, wherein each of the first and second staple cartridges includes a staple pusher extending longitudinally thereacross, and when the first and second jaws are in the closed position, the longitudinally extending rib engages the staple pusher to expel the staples from the respective first and second staple cartridges.

16. The end effector of claim 14, wherein each of the first and second jaws includes a pair of openings defined in the outer surface of the body on opposed sides of the longitudinally extending rib.

17. The end effector of claim 16, wherein each of the first and second staple cartridges includes side walls having a pair of raised edges extending upwardly from the cartridge body on opposed sides of the staple pusher, the pair of raised edges extending through the pair of openings of the body of the respective first and second jaws.

18. The end effector of claim 10, wherein each of the first and second jaws includes an inner surface, and when the first and second jaws are in the open position, the tissue facing surface of each of the first and second staple cartridges is offset from the inner surface, and when the first and second jaws are in the closed position, the tissue facing surface is flush with the inner surface.

\* \* \* \* \*